United States Patent [19]

Shihata

[11] Patent Number: 4,858,624
[45] Date of Patent: Aug. 22, 1989

[54] DEVICE AND METHOD FOR INTRAVAGINAL, BARRIER-TYPE PREVENTION OF CONCEPTION AND INFECTION

[75] Inventor: Alfred A. Shihata, Bonita, Calif.

[73] Assignee: Vance Products Incorporated d/b/a/ Cook Urological Incorporated and Cook OB/GYN, Spencer, Ind.

[21] Appl. No.: 159,846

[22] Filed: Feb. 24, 1988

[51] Int. Cl.$^4$ .............................................. A61F 5/46
[52] U.S. Cl. .................................. 128/834; 128/837; 128/838
[58] Field of Search ........ 128/830, 832, 834, 835–837, 128/841, 840, 838

[56] References Cited

U.S. PATENT DOCUMENTS

| | | | |
|---|---|---|---|
| 1,634,555 | 7/1927 | Peldubet | 128/834 X |
| 1,949,863 | 3/1934 | Hay | 128/837 |
| 2,071,248 | 2/1937 | Campbell | 128/837 |
| 2,104,275 | 1/1938 | Schleicher | 128/838 |
| 2,110,962 | 3/1938 | Munro | 128/832 X |
| 2,157,689 | 5/1939 | Clark Jr. | 128/837 |
| 2,218,009 | 10/1940 | Schmitz Jr. | 128/838 |
| 2,324,656 | 7/1943 | Vincent | 128/837 |
| 2,443,943 | 8/1945 | Young | 128/837 |
| 2,625,154 | 1/1953 | Young | 128/837 |
| 2,638,896 | 7/1953 | Clark | 128/837 |
| 2,664,082 | 12/1953 | Heuboski et al. | 128/837 |
| 2,676,589 | 4/1954 | Heuboski et al. | 128/837 |
| 2,823,669 | 2/1958 | Kunnas Jr. | 128/837 |
| 3,128,762 | 4/1964 | Young | 128/834 |
| 3,130,721 | 4/1964 | Young | 128/837 |
| 4,031,886 | 6/1977 | Morhenn | 128/837 |
| 4,286,593 | 9/1981 | Place et al. | 128/832 |

OTHER PUBLICATIONS

"Conventional Methods of Contraception: Condom, Diaphragm, and Vaginal Foam", from Clinical Obstetrics and Gynecology, vol. 17, No. 1, Mar. 1974, pp. 21–33.

"The Diaphragm and Other Intravaginal Barriers", from Population Reports, Series H, Number 4, Jan. 1976, pp. H-57 through H-74.

"Contraception Update", from Consultant, vol. 27, No. 11, Nov. 1987, pp. 23–32.

Primary Examiner—Robert A. Hafer
Assistant Examiner—Kevin G. Rooney
Attorney, Agent, or Firm—Baker, Maxham, Jester & Meador

[57] ABSTRACT

A device and method for intravaginal, barrier-type prevention of conception and infection by sexually-transmitted diseases based upon a barrier-type device including a flexible cervical dome having a continuous fornical rim defining an opening into the dome and a continuous, annular, vaginal brim which circumscribes and is attached to the cervical dome at the fornical rim. The vaginal brim is reverse-folded from the fornical rim, and has a dimension which continuously increases with circumferential symmetry from an anterior vaginal extension of the brim to a posterior vaginal extension of the brim which is diametrically opposite the anterior vaginal extension. The fornical rim is characterized in having a lip which extends inwardly from the opening toward the centerline of the dome. The brim has a curvature in a direction away from the dome.

4 Claims, 3 Drawing Sheets

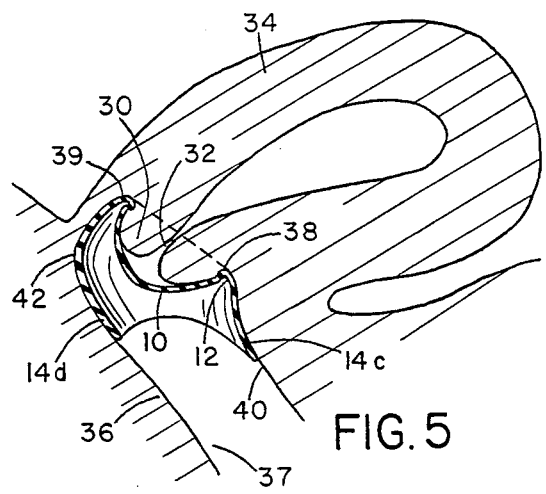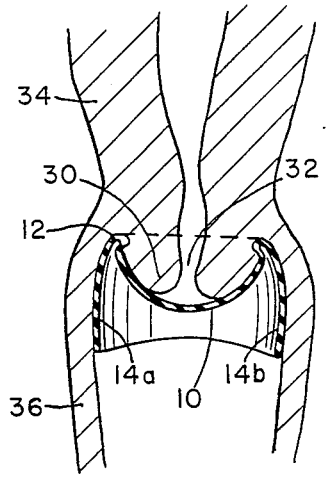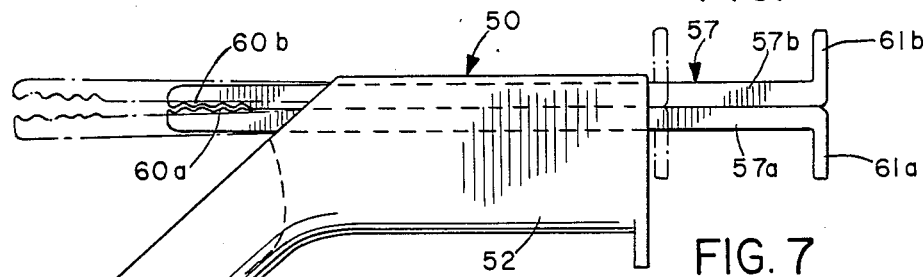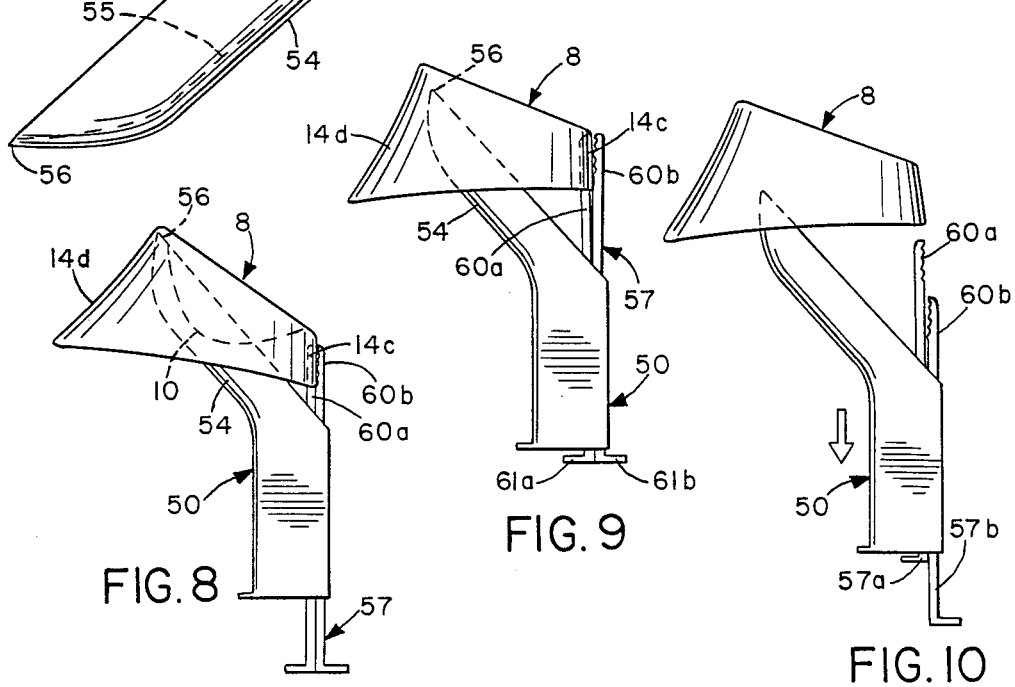

4,858,624

DEVICE AND METHOD FOR INTRAVAGINAL, BARRIER-TYPE PREVENTION OF CONCEPTION AND INFECTION

BACKGROUND OF THE INVENTION

The invention concerns contraception and the prevention of sexually-transmitted diseases by means of a barrier-type device and further concerns a barrier-type device which engages the cervix by extending into the fornices and seals circumferentially against the vagina in the vicinity of the cervix.

The prior art devices for intravaginal, barrier-type prevention of conception and sexually transmitted disease include the diaphragm and the cervical cap. The diaphragm, when seated intravaginally, acts as a barrier to prevent sperm from entering the os of the cervix. A spermicide is used on the inside of the diaphragm to kill sperm traversing over the edge of the diaphragm. Characteristically, the diaphragm is a shallow rubber cup with a rim. A round, coiled metal spring is disposed in the rim. The diaphragm is intended for intravaginal disposition between the posterior aspect of the pubic bone and the posterior fornix. When thus seated, the diaphragm presses against the vaginal wall to form a continuous barrier therewith.

The cervical cap is a small, vaulted or domed device, more rigid than the diaphragm, and dimensioned to fit over a cervix, where it is retained by suction, rather than spring tension as is the diaphragm. The cap includes a dome which rises from a rim. The cap is slipped over the cervical protrusion to block access to the uterus through the cervical os.

None of these barrier-type devices is adapted to fit in close anatomical sealing engagement between the vagina and the cervix. The diaphragm is held against the upper part of the vaginal canal by the tension of the spring in its rim, while the cervical cap typically engages only the tip of the cervix. Both of these devices can be dislodged by sexual arousal, coital activity, or orgasm. As is known, such dislodgment can reduce the effectiveness of the barrier and permit unintended fertilization or unwanted infection, or worse, both.

In failing to take into account the anatomy and physiology of the vagina and the cervix, the prior art barrier-type devices form imperfect barriers against the penetration of sperm and agents of sexually transmitted diseases into the uterus. As is known, fertilization and infection take place within the uterus, therefore the more sound the barrier to the cervical os, the greater the likelihood of preventing such fertilization or infection. With the emergence of the AIDS (acquired immune deficiency syndrome) epidemic, the risk of life-threatening infection accompanying heterosexual activity is increasing steadily. Therefore, there is a compelling need for intravaginal, barrier-type devices which can substantially decrease the risk of infection by significantly increasing the effectiveness and reliability of the barrier to entry of bodily fluids such as semen, into the cervix.

Accordingly, it is an urgent objective of the invention to provide an intravaginal, barrier-type device which accounts for, and takes advantage of, the anatomy and physiology of the vagina in the vicinity of the cervix to form a more perfect, and a more reliable, seal against the movement of sperm and micro organisms from the vaginal canal through the cervical os into the uterus.

A significant advantage of such a device is the simultaneous reduction of the prospects of conception.

SUMMARY OF THE INVENTION

The invention is based upon the inventor's critical observation that a barrier-type device engaging the cervix and the vagina by seating at the bottom of the fornices and then folding back from the fornices along the interior vaginal walls provides a barrier adapted to the anatomy and physiology of the vagina in the vicinity of the cervix which not only forms a reliable, effective seal, but also resists displacement during arousal, inercourse, and orgasm.

The device conforms to and sealingly engages the vagina in the vicinity of the cervix. The sealing engagement of the device with the vagina is continuous during all of the expected physiological changes which the vagina and cervix undergo as the result of, for example, sexual activity and menstrual cycle.

From its structural aspect, the invention is a barrier-type device for preventing conception and infection by sexually transmitted diseases, which includes a cervical dome fabricated from a flexible, physiologically nonreactive material, which has an opening and a curved surface extending from the opening to a dome peak. The dome transitions to a continuous fornical rim, the rim defining the opening of the dome. The rim transitions through a backward fold against the dome to a continuous, annular, vaginal brim circumscribing the dome.

Preferably, the vaginal brim has a dimension which continuously increases with circumferential symmetry from an anterior vaginal extension to a posterior vaginal extension diametrically opposite the anterior vaginal location.

The device further includes an inwardly-turned, annular lip on the rim which juts into the opening. The lip, rim, and dome form an annular trapping groove between the brim and the dome.

From another aspect, the invention is a method of preventing conception and infection by sexually transmitted diseases with a barrier-type device having a cervical dome which transitions to a fornical rim defining an opening in the dome, the rim transitioning by a backward fold to a vaginal brim circumscribing the dome and extending from the rim toward the top of the dome. The method includes steps of applying a spermicide to the device and placing the device in an intravaginal, blocking position which situates the dome in a cervical blocking position, and in which the rim is fornically engaged and the brim is in a continuous, sealing vaginal engagement.

In the method, the vaginal brim has a dimension which continuously increases with circumferential symmetry from an anterior vaginal location on the brim to a posterior vaginal location on the brim diametrically opposite the anterior vaginal location, the method further including the step of orienting the device to place the anterior vaginal location in an anterior vaginal engagement and the posterior vaginal location in a posterior vaginal engagement.

The invention is also found in the combination of an intravaginal, barrier-type device for preventing conception and infection by sexually-transmitted diseases including a device, fabricated from a flexible physiologically nonreactive material, and having a cervical dome with an opening defined by a rim and a curved surface extending to a dome peak and further including, transitioning by a backward fold from the rim, a continuous, annular vaginal brim circumscribing, and attached to, the cervical dome at the rim, and having a dimension which continuously increases with circumferential symmetry from an anterior vaginal location on the brim to a posterior vaginal location on the brim. An applicator for placing the device in operational disposition includes a speculum-type lower body with a main member that transitions to an angled member with an edge for engaging the barrier-type device between the brim and the dome at the posterior fornical location. The insertion device further includes a mechanism, slidably disposed in the main member for releasably engaging the vaginal brim at the anterior vaginal location.

One will appreciate how the summarized invention achieves the above-stated objectives when the detailed description is read with reference to the below-described drawings, in which:

FIG. 5 is a partial, sagittal section of female sexual anatomy showing, in schematic representation, the posterior aspect of the vaginal tract and the barrier-type device in place covering the cervix, and sealing to the posterior of the vaginal canal;

FIG. 6 illustrates a schematic of the posterior of the vaginal canal from a frontal aspect showing the barrier-type device in place;

FIGS. 7-10 illustrate the structure and operation of the applicator for insertion of the barrier-type device of FIGS. 1-6 into the vagina.

DETAILED DESCRIPTION OF THE PREFERRED EMBODIMENT

Figure 1:
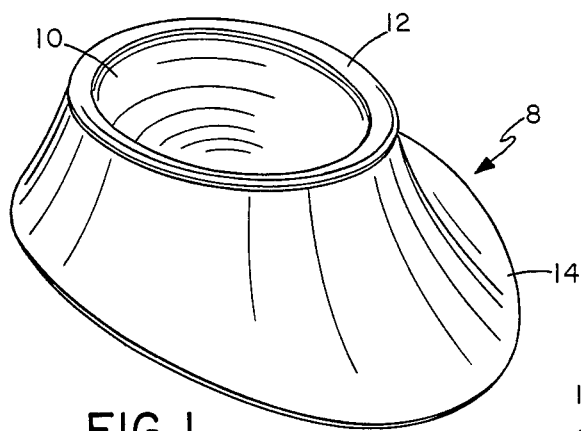
FIG. 1 illustrates a perspective view of the barrier-type device of the invention.
Figure 2:
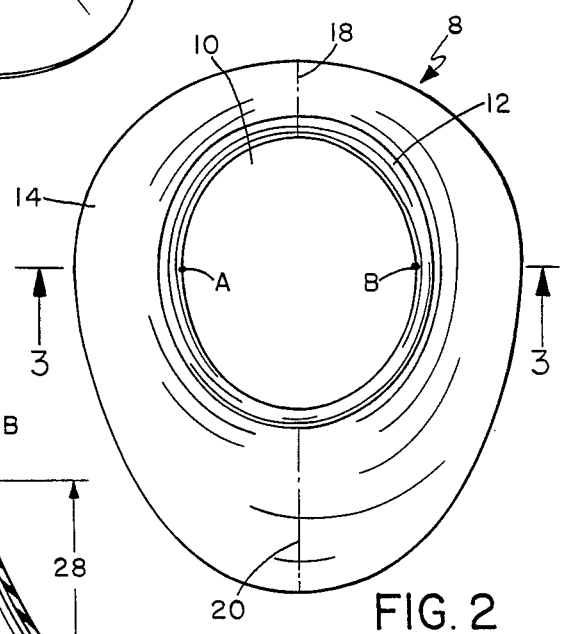
FIG. 2 is a plan view of the device.
Figure 3:
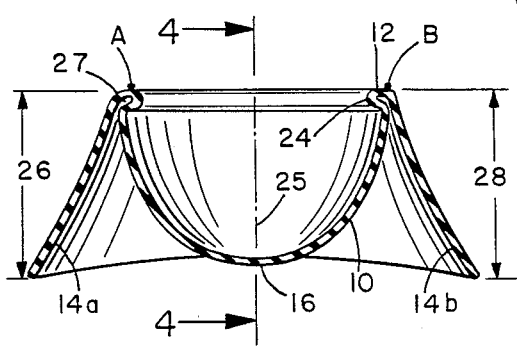
FIG. 3 is a sectional view of the device taken along lines 3—3 of FIG. 2.
Figure 4:
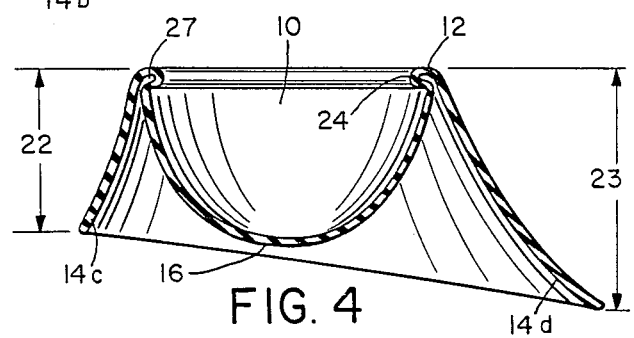
FIG. 4 is a sectional view, rotated 90 from FIG. 3, and taken along lines 4—4 of FIG. 3.

An intravaginal, barrier-type device for preventing conception and infection by sexually-transmitted diseases is illustrated structurally in FIGS. 1-4. Preferably, the device is a single piece formed by molding a flexible, physiologically non-reactive material, such as latex rubber. The device 8 includes a cervical dome 10. The dome preferably has a hemi-spherical or hemi-ovoid shape which forms a cervical enclosure. At the opening of the enclosure, the dome 10 transitions to a fornical rim 12, which in turn, transitions by a backward fold to a vaginal brim 14. As best seen in FIGS. 3 and 4, the dome has a peak, or top, 16.

As FIGS. 1-4, reveal, the vaginal brim circumscribes, or surrounds, the dome and extends upwardly from the rim 12. The brim exhibits lateral symmetry, as illustrated in FIG. 3, where the lateral extensions 14a and 14b of the brim 14 are substantially equal in form and dimension. The width of the brim increases continuously from the anterior to the posterior of the device 8. This increase is revealed in FIGS. 1 and 4. In FIG. 4, the anterior extension 14c of the brim 14 has a smaller dimension 22 than the dimension 23 at the posterior extension 14d of the brim 14. The brim also has an outward bias, or curve, to it, as is seen in FIGS. 1, 3, and 4.

The width of the brim increases with circumferential symmetry from an anterior vaginal location 18 on the anterior extension 14c of the brim to a posterior vaginal location 20 on the posterior portion 14d of the brim. The circumferential symmetry of the brim 14 is illustrated in FIG. 2. In FIG. 2, point A over the lateral extension 14a is displaced in a counterclockwise direction on the rim 12 from the anterior vaginal location by a rim segment equal to the rim segment by which the point B over the lateral extension 14b is displaced on the rim 12 clockwise from the anterior vaginal location 18. As shown in FIG. 3, the dimension 26 reflecting the width of the brim at extension 14a is equal to the dimension 28 reflecting the width of the brim at extension 14b.

An annular lip 24 is formed in the device 8 by an inward extension of the rim 12 along the periphery of the opening into the dome 10. The lip 24 juts into the opening toward the center line 25 of the dome 10. The backward fold of the rim 12 at the lip 24 by which the rim 12 transitions to the brim 14 forms an annular groove 27 between the brim 14 and dome 10.

The significance of the structure of the barrier-type device 8 is illustrated in FIGS. 5 and 6. In FIGS. 5 and 6, female anatomy is conventionally illustrated as including a cervix 30 through which the cervical os 32 opens to the interior of the uterus 34. The vagina 36 includes an inner surface 37 which transitions to the cervix 30 by way of a fornix, an anatomical fold or recess. As is known, the fornix increases in depth from its anterior to its posterior aspects, which are usually referred to as the anterior fornix 38 and the posterior fornix 39, respectively. Further, at its rear, the vagina 36 transitions, by way of the anterior vaginal wall 40 to the anterior fornix 38, and by way of the posterior vaginal wall 42 to the posterior fornix 39. As shown in the frontal cross section of FIG. 6, the fornix is laterally symmetrical.

FIGS. 5 and 6 illustrate how the barrier-type device of FIGS. 1-4 is adapted to the anatomy and physiology of the vagina in the vicinity of the cervix. As shown in FIG. 5, the proper orientation of the device 8 finds the cervical dome 10 engaging the cervix, which extends through the opening defined by the rim 12. The rim is seated at the bottom of the fornices. The annular lip 24 grips the bottom of the cervix at the fornices, thereby forming a circumferential seal. The brim 14 extends from the bottom of the fornices in close sealing engagement with the walls of the vagina, thereby continuing the circumferential seal along the vagina forwardly from the fornices. The barrier-type device is oriented with respect to the cervix to place the anterior extension 14c against the anterior vaginal wall 40, in the vicinity of the anterior fornix. Similarly, the posterior extension 14d is oriented to engage the posterior vaginal wall 42 in the vicinity of the posterior fornix. As shown in FIG. 6, the orientation of FIG. 5 disposes the lateral rim extensions 14a and 14b against the lateral vaginal walls in the vicinity of the lateral fornices.

As shown in FIGS. 5 and 6, not only does the device seal to the vagina and cervix, it orients the annular groove 27 toward the opening of the vagina. Thus oriented, the groove 27 will trap fluids traveling along the inside of the brim 14 toward the dome 10.

In use, a spermicide such as NONOXYNOL-9, is applied to the total surface of the device 8, and the device is inserted into the vagina to engage the cervix with the orientation illustrated in FIGS. 5 and 6. Thus, seated, the barrier-type device of the invention will seal from the base of the cervix, in the fornices and continuously and circumferentially along the vagina. This seal is superior to the prior art barrier devices. As is known, the diaphragm would engage only the posterior fornix, extending across the top of the vaginal wall forward of the anterior of the cervix. The cervical cap engages only the top of the cervix, and, generally, does not extend fully into the posterior, anterior, and lateral fornices. However, the device 8 fits precisely to the anatomy and physiology of the vagina in the vicinity of the cervix. Such an ananatomically adapted form will not only seal effectively when the device is seated, but will also seal reliably by resisting unintentional displacement or dislodgment. The device is retained in place by suction exerted in the cervix by the dome 10, by the grip exerted on the base of the cervix by the annular lip 24, by a snug fitting between the rim 12 of the fornices, and by the outward curve of the brim, which flattens against the vagina. All of these mechanisms help prevent dislodgment of the device and contribute to the seal which the device makes.

An applicator for intravaginal placement of the barrier-type device 8 is illustrated in FIGS. 7–10. The applicator 50 consists of a speculum-type portion with a main body, or a handle, 52 which transitions into a projection 54 having an angle of, preferably, 40 with the main body 52. As seen in FIG. 7, the angled projection 54 has a concave recess 5. A rounded forward edge 56 is provided on the distal end of the projection 54. A movable inserter 57 is slidably disposed in the main portion 52 and moved in the main portion between a first position, indicated by the solid lines in FIG. 7, and a second, release, position denoted in FIG. 7 by the interrupted lines. The inserter 57 consists of two equivalent elongate pieces 57a and 57b having serrated forward faces 60a and 60b and rear flanges 61a and 61b, respectively. The applicator 50 is formed from a physiologically inert material, such as a relatively rigid plastic, and has all of its edges and ends smoothed and rounded to reduce the prospect of injuring the vagina during placement of the device 8.

FIGS. 8–10 illustrate how the applicator is used to place the barrier-type device 8. As shown in FIG. 8, the barrier-type device is carried on the applicator by engagement of the forward end 56 in the groove 27 of the device 8 formed between the dome 10, the rim 12, and the posterior vaginal extension 14d. The brim 14 is grasped between the serrated surfaces 60a and 60b at the anterior vaginal extension 14c. The inserter 57 is retracted to the first position. In this position, the serrated faces 60a and 60b are forced together with the anterior vaginal extension 14c grasped between them. As the inserter 57 is drawn backward to the first position, the barrier-type device is stretched and retained on the applicator 50 by the tension of the flexible material from which the device 8 is formed. Thus arranged, the barrier-type device on the applicator 50 is placed intravaginally, with the device oriented as in FIG. 5.

After traversing the vaginal canal, the end 56 of the applicator 50 will place the posterior vaginal extension 14d of the brim against the posterior vaginal wall and seat the rim 12 in the posterior fornix 39. When this occurs, the anterior vaginal extension 14c will still be forward of the anterior fornix 38. Next, the inserter 57 is slid forwardly in the main body 52 to the second position, which will move the anterior vaginal extension 14c into engagement with the anterior fornix 38. When this occurs, the barrier-type device 8 will be retained in the engagement of FIG. 5 by the mechanisms described above.

Removal of the applicator can be understood with reference to FIGS. 9 and 10. When the barrier-type device is seated by forward movement of the inserter 57, the flexibility of the members 57a and 57b will cause the serrated faces 60a and 60b to spring apart slightly. Next, with the barrier-type device retained in position by suction, the upper member 57b is moved rearwardly toward the first position, which disengages the inserter from the anterior vaginal extension 14c of the brim. The lower member 57a is then pulled rearwardly. This completely disengages the applicator 52 from the anterior fornical extension 14c of the brim, and permits the applicator 52 to be removed.

Figure 11:
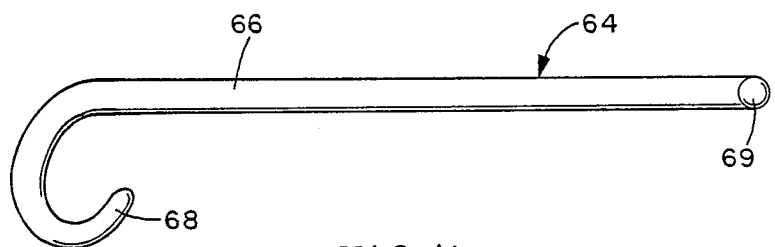
FIGS. 11 and 12 illustrate an extractor for removal of the barrier-type device from intravaginal placement.
Figure 12:
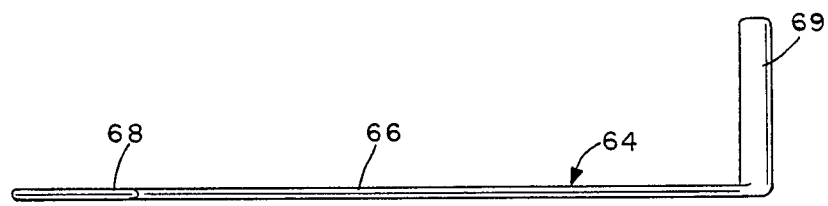

As shown in FIGS. 11 and 12, an extractor 64 has an elongate portion 66 with a cross section substantially flattened in a plane. The distal tip of the elongate portion 66 transitions to a hook 68. The hook curves backwardly over the elongate portion and is flattened in the same plane. An operating handle 69 is attached to the proximal end of the portion 66, to be substantially perpendicular to the plane of flattening of the portion and hooks.

The barrier-type device 8 is extracted by insertion of the elongate portion 66, hook first, flat into the vagina in the direction of the anterior fornix. When the anterior fornix is encountered, the extractor is rotated 90, by the handle, to bring the hook 68 into engagement with the back of the brim 12 at the anterior vaginal location. The extractor is pulled out, bringing the device 8 with it.

Obviously, many modifications and variations of the present invention are possible in light of the above teachings, and it is therefore understood that within the scope of the disclosed inventive concept, the invention may be practiced other than as specifically described.

I claim:

1. A barrier-type device for preventing conception and infection by sexually-transmitted diseases, comprising:

a cervical dome fabricated from a flexible, physiologically non-reactive material, said dome having an opening and a curved surface extending from said opening to a dome top;

a continuous fornical rim on said dome, said rim defining said opening; and a continuous, annular vaginal brim circumscribing said cervical dome, said vaginal brim being folded at said rim outwardly and downwardly with respect to said opening; and wherein the vertical dimension between the rim and the outside edge of the brim increases with circumferential symmetry from an anterior vaginal location on said brim to a posterior vaginal location on said brim which is opposite said anterior vaginal location.

2. The barrier-type device of claim 1 further including an annular lip on said rim, said annular lip extending inwardly from said rim toward a centerline of said dome, and an annular groove between said vaginal brim and said dome, said annular groove being formed by an outward fold of said vaginal brim at said annular lip.

3. A method of preventing conception and infection by sexually transmitted disease with a barrier-type device having a cervical dome with a fornical rim defining an opening in said dome and a vaginal brim circumscribing said dome, said vaginal brim being folded at said rim outwardly and downwardly with respect to said opening, and said brim having a vertical dimension between the rim and the outside edge of the brim which increases with circumferential symmetry from an anterior vaginal brim extension to a posterior vaginal brim extension which is diametrically opposite said anterior vaginal brim extension, said method including:

applying a spermicide to said vaginal brim and to said dome;

placing said device in an intravaginal engagement which situates said dome in a cervical engagement with said fornical rim fornically engaged, and said vaginal brim in a continuous, sealing vaginal engagement; and, orienting said device to place said anterior vaginal brim extension in an anterior vaginal engagement and said posterior vaginal brim extension in a posterior vaginal engagement.

4. A kit for intravaginal, barrier-type prevention of conception and sexually-transmitted infection, comprising, in combination:

a barrier-type device including:

a cervical dome fabricated from a flexible, physiologically non-reactive material, said dome having an opening and a curved surface extending from said opening to a dome top;

a continuous fornical rim on said dome, said rim defining said opening; and a continuous, annular vaginal brim circumscribing said cervical dome and folded at said rim outwardly and downwardly with respect to said opening; and an applicator including:

a lower body with a main member and a projection attached at an angle to said main member, said projection including a concave recess and an edge for engaging said barrier-type device between said vaginal brim and said dome; and an inserter, slidably disposed in said main member for being moved to a first, retracted position for engaging said vaginal brim and to a second, extended position for disengaging said vaginal brim.

* * * * *